United States Patent
Zheng et al.

(10) Patent No.: US 10,928,282 B2
(45) Date of Patent: Feb. 23, 2021

(54) METHOD AND DEVICE FOR DETERMINING ELASTICITY OF CEMENT STONE UTILIZED IN WELL CEMENTING OF OIL-GAS WELL

(71) Applicant: PetroChina Company Limited, Beijing (CN)

(72) Inventors: Youzhi Zheng, Beijing (CN); Bo Kong, Beijing (CN); Jie Li, Beijing (CN); Huiyun Ma, Beijing (CN); Yu Sang, Beijing (CN); Tao Yang, Beijing (CN); Minghua Xie, Beijing (CN); Libin Jiao, Beijing (CN); Fuyun Wang, Beijing (CN); Hongwei Xia, Beijing (CN); Jiang Yu, Beijing (CN); Qiyan Tan, Beijing (CN); Congjing Liu, Beijing (CN); Ji Chen, Beijing (CN); Qiang Fu, Beijing (CN); Xiaoli Zhao, Beijing (CN); Fenglin Guo, Beijing (CN); Yong Wu, Beijing (CN); Yiguo He, Beijing (CN); Bin Wang, Beijing (CN); Xiaojiao Wang, Beijing (CN)

(73) Assignee: PetroChina Company Limited, Beijing (CN)

( * ) Notice: Subject to any disclaimer, the term of this patent is extended or adjusted under 35 U.S.C. 154(b) by 0 days.

(21) Appl. No.: 16/079,791

(22) PCT Filed: Oct. 31, 2017

(86) PCT No.: PCT/CN2017/108471
§ 371 (c)(1),
(2) Date: Aug. 24, 2018

(87) PCT Pub. No.: WO2018/099228
PCT Pub. Date: Jun. 7, 2018

(65) Prior Publication Data
US 2019/0271621 A1 Sep. 5, 2019

(30) Foreign Application Priority Data

Nov. 30, 2016 (CN) .......................... 201411087894.8
Jul. 24, 2017 (CN) .......................... 201710605203.7

(51) Int. Cl.
*G01N 3/08* (2006.01)
*G01N 3/02* (2006.01)
*G01N 33/38* (2006.01)

(52) U.S. Cl.
CPC ............... *G01N 3/08* (2013.01); *G01N 3/02* (2013.01); *G01N 33/383* (2013.01)

(58) Field of Classification Search
CPC ........... G01N 3/08; G01N 3/02; G01N 33/383
(Continued)

(56) References Cited

U.S. PATENT DOCUMENTS

2013/0228019 A1 9/2013 Meadows et al.
2014/0352949 A1 12/2014 Amendt et al.

FOREIGN PATENT DOCUMENTS

CN 101718655 A 6/2010
CN 102401769 A 4/2012
(Continued)

OTHER PUBLICATIONS

Translation of International Search Report, PCT/CN2017/108471, PetroChina Company Limited, 2 pages (dated Jan. 26, 2018).
(Continued)

*Primary Examiner* — Jamel E Williams
(74) *Attorney, Agent, or Firm* — Foley & Lardner LLP

(57) ABSTRACT

The invention provides a method and device for measuring the elasticity of hardened cement for cementing of oil-gas wells. The measurement method comprises: determining the loading and unloading rates of the hardened cement; determining the maximum loading on the hardened cement;
(Continued)

determining the experimental temperature and the experimental pressure of the hardened cement; establishing a stress-strain curve for the hardened cement; and describing the elasticity of the hardened cement with the degree of strain recovery of the hardened cement in different cycles, and describing the mechanic integrity of the hardened cement with the degree of damage to the hardened cement in different cycles. The invention further provides a device for measuring the elasticity of hardened cement for cementing of oil-gas wells. The measurement method and device of the present invention provide a universal comparing platform for research on hardened cement modification as well as examination of domestic and foreign special cement slurry systems, which is of great significance in evaluation of well hole integrity and well life.

7 Claims, 6 Drawing Sheets

(58) Field of Classification Search
USPC .......................................................... 73/799
See application file for complete search history.

(56) References Cited

FOREIGN PATENT DOCUMENTS

| CN | 102866061 A | 1/2013 |
|----|-------------|--------|
| CN | 103278389 A | 9/2013 |
| CN | 203201545 A | 9/2013 |
| CN | 103558363 A | 2/2014 |
| CN | 104181287 A | 12/2014 |
| CN | 104335037 A | 2/2015 |
| CN | 104849134 A | 8/2015 |
| CN | 105784482 A | 7/2016 |
| CN | 106092688 A | 11/2016 |

OTHER PUBLICATIONS

English-language translation of Chinese Office Action, PetroChina Company Limited, 7 pages (dated Dec. 19, 2019).
Li et al., "Improvement of latex on mechanical deformation capability of cement sheath under triaxial loading condition," Acta Petrolei Sinica, vol. 28, No. 4, 4 pages (Jul. 2017).
English-language translation of First Office Action and Search Report, Chinese Patent App. No. 201710605203.7 (dated Jul. 3, 2019).
Chinese Search Report, PetroChina Company Limited, 5 pages (dated Jul. 7, 2017).

*ENGLISH-LANGUAGE TRANSLATION OF INTERNATIONAL APPLICATION*

*ENGLISH-LANGUAGE TRANSLATION OF INTERNATIONAL APPLICATION*

*ENGLISH-LANGUAGE TRANSLATION OF INTERNATIONAL APPLICATION*

*ENGLISH-LANGUAGE TRANSLATION OF INTERNATIONAL APPLICATION*

*ENGLISH-LANGUAGE TRANSLATION OF INTERNATIONAL APPLICATION*

METHOD AND DEVICE FOR DETERMINING ELASTICITY OF CEMENT STONE UTILIZED IN WELL CEMENTING OF OIL-GAS WELL

CROSS-REFERENCE TO RELATED APPLICATIONS

This application is a U.S. National Stage Application of International Application No. PCT/CN2017/108471, filed Oct. 31, 2017, which claims the benefit of and priority to Chinese Patent Application No. 201611087894.8, filed Nov. 30, 2016, and also to Chinese Patent Application No. 201710605203.7, filed Jul. 24, 2017, all of which are incorporated herein by reference in their entireties.

TECHNICAL FIELD

The invention relates to a measurement method and device, particularly to a method and device for measuring elasticity of hardened cement for well cementing, pertaining to the field of oil-gas field exploitation.

BACKGROUND

Annular pressure is the primary safety issue in the development and production of complex natural gas wells, which is universally present all over the world. In the outer continental shelf (OCS) area of the Gulf of Mexico, there are approximately 15,500 production wells, closed wells, and temporarily abandoned wells. Statistics conducted by the US Minerals Management Service (MMS) on the wells in this area show that 6,692 wells (about 43%) have at least one layer of casing with annular pressure. In these wells with annular pressure, there are 10,153 layers of casings with annular pressure, among which 47.1% are production casings, 16.3% are intermediate casings, 26.2% are surface casings, and 10.4% are conductor casings. For the majority of the wells in this area, several layers of casing columns are placed downhole, making it difficult to determine the causes of annular pressure and take pertinent remedial actions, resulting in remedy cost of up to 1 million dollars per well. In Canada, annular pressure is present in various types of wells. Annular pressure issues exist to various degrees in the shallow gas wells in South Alberta, the heavy oil wells in Eastern Alberta, and the deep gas wells in the foothills of the Rocky Mountains. The annular pressure issues in Canada mostly result from the surging of gas to the wellhead due to poor annulus sealing.

Currently, in high-temperature deep wells in China, such as some of the gas wells in the Kela gas field in Tarim and the Luojiazhai gas field in Sichuan, annular pressure is present to various degrees, which eventually affect a high and stable yield of these gas wells. The $H_2S$ content in the gas reservoir of Feixianguan formation in the gas fields such as Luojiazhai, Dukouhe, Tieshanpo, and Wolonghe is mostly 10% to 15%, while the $H_2S$ content in the gas reservoir in the Longgang gas field is mostly at 30 to 180 g/m³. A high level of $H_2S$ not only causes serious corrosion to the high-strength steel downhole and on the ground, but also has high toxicity, which is a direct threat to human safety, making the drilling and completion of wells highly risky.

For the annular pressure issue in the intermediate casings in sulfur-containing gas wells caused by the quality of cement sheath for well cementing, the erosion of acidic media to the cement sheath is a minor factor, while the major factors that lead to gas surging from the cement sheath are the mechanical damage to the cement sheath during construction and the quality of the cement slurry. Therefore, during the cementing of gas wells, follow-up evaluation of the cement slurry performance and assessment of the mechanic integrity of the cement sheath in a late stage are critical to safe development of gas wells.

As a matter of fact, during the development of each oil-gas well, there is always an issue concerning long-term sealing and separation performance of the cement sheath, which issue is caused by alternating pressure within the shaft, for example, alternating force before and after pressure testing, in sustained drilling, or during well shut-in and production. On this account, the concept of tough cement has been coined. Maintaining good toughness of a cement sheath allows the cement sheath more space to undergo elastic deformation than common cement under the pressing force from the internal casing and the external pressure from the formation, and leaves no microgaps at the interface under various types of force, so that the long-term sealing and separation ability of the cement sheath for well cementing lasts longer, which is of great significance for assessing shaft safety and prolonging the lifetime of oil-gas wells. Tough cement systems will become a mainstream direction in the future development of well cementing in the petroleum engineering industry.

Tough cement, also known as flexible cement, elastic cement, or the like, means that the cement has greater deformation capacity than regular cement for oil wells under the same stress, and its primary mechanical characteristics lie in a remarkably lower Young's modulus than regular cement for oil wells, and similar compressive strength and tensile strength.

Currently, there is no unified standard test for the Young's modulus of hardened cement in China or abroad. The mechanic test for the tri-axial stress of hardened cement is conducted mainly with reference to the standards for testing the mechanic properties of rocks.

The testing method for oil-well cement (GB/T 19139-2012) specifies measurement methods for application properties of oil-well cement, including density, compressive strength, non-destructive acoustic wave testing, thickening time, static water loss, permeability, rheology, gel strength, stability, downhole fluid compatibility and the arctic grout test method, as well as calculating methods for the pressure drop and flow pattern of cement slurry in casings and annulus, but does not mention any measurement standard for the mechanical deformation ability in terms of elasticity/toughness/flexibility of oil-well cement.

Mechanic properties under tri-axial stress of the same hardened cement for cementing of oil-gas wells (2.25 g/cm³) were measured in different laboratories, and the results showed that: due to the different loading rates adopted in the laboratories, the resultant mechanic parameters were very different, particularly the Young's modulus, which varies by up to one order of magnitude over the test data. Furthermore, the Young's modulus of the hardened cement varies over different intervals in the stress-strain curve. Accordingly, the same hardened cement may exhibit various values of the Young's modulus, or the measured value of the Young's modulus of the hardened cement has poor reproducibility and cannot reflect the mechanic nature of the hardened cement, which inevitably makes it difficult to precisely evaluate the integrity of hardened cement in downhole settings or even the integrity of the entire well hole.

Therefore, it is necessary to study the measurement of mechanic properties of hardened cement in order to address the problems present in measurement of the Young's modulus of the hardened cement.

SUMMARY

To solve the above technical problems, an objective of the invention is to provide a measurement method and a measurement device that can objectively indicate the elasticity of hardened cement downhole.

To achieve the above technical objective, the present invention provides a method for measuring the elasticity of hardened cement for cementing of oil-gas wells, the method comprising the steps of:

determining the loading and unloading rates of the hardened cement, according to the force applied on the hardened cement and the duration required for the loading and unloading of the force, in various engineering operations;
  establishing a normal stress-strain curve, and determining the maximum loading on the hardened cement by comparing the data of the force applied on the hardened cement in the various engineering operations to the normal stress-strain curve;
  determining the experimental temperature and the experimental pressure, and establishing a stress-strain curve for the hardened cement by conducting a multi-cycle tri-axial stress test on the hardened cement at the experimental temperature and the experimental pressure based on the determined loading rate, unloading rate and maximum loading of the hardened cement; and
  quantitatively describing the elasticity of the hardened cement with the degree of strain recovery of the hardened cement in different cycles, and qualitatively describing the mechanic integrity of the hardened cement with the degree of damage to the hardened cement in different cycles, so as to complete the assessment of the elasticity of the hardened cement for cementing of oil-gas wells.

The measurement method according to the present invention is applicable in any engineering operation to determine different loading rates, unloading rates, and maximum loadings. The various engineering operations refer to all sorts of engineering operations performed in oil-gas wells after cementing, such as processes of pressure testing, drilling, acidification, fracturing, and the like.

In the method for measuring the elasticity of hardened cement for cementing of oil-gas wells according to the present invention, it is preferred to prepare an experimental sample of hardened cement, prior to the measurement of the elasticity of the hardened cement for cementing of oil-gas wells, the preparing comprising the steps of:

preparing an experimental cement slurry, setting and hardening it into hardened cement by curing the cement slurry under a simulated temperature and pressure condition for hardened cement for a designated period of time according to the downhole environment surrounding the hardened cement, and processing the hardened cement to a standard core size to obtain the sample of hardened cement.

In the method for measuring the elasticity of hardened cement for cementing of oil-gas wells according to the present invention, the loading and unloading rates of the hardened cement are determined according to the force applied on the hardened cement and the duration required for loading and unloading of the force in various engineering operations by using analytical software ("*Software System for Analysis of Formation Cement Sheath Mechanics*", Chinese Software Writing Registration No. 0910640) in connection with actual situations in the engineering operations.

In the method for measuring the elasticity of hardened cement for cementing of oil-gas wells, preferably, the normal stress-strain curve is established through a tri-axial stress test.

In the method for measuring the elasticity of hardened cement for cementing of oil-gas wells, preferably, determining the maximum loading on the hardened cement comprises the step of: determining the average value of the maximum strains of the hardened cement, and determining the maximum loading as the stress value corresponding to the maximum strain according to the normal stress-strain curve.

In the method for measuring the elasticity of hardened cement for cementing of oil-gas wells, preferably, the experimental temperature and the experimental pressure are determined in accordance with the downhole depth of the hardened cement.

In the method for measuring the elasticity of hardened cement for cementing of oil-gas wells, preferably, the degree of strain recovery of the hardened cement in different cycles is determined according to the following equation:

$$(\text{maximum strain upon loading} - \text{minimum strain upon unloading})/\text{maximum strain upon loading};$$

wherein the resultant value is the degree of strain recovery of the hardened cement, and a higher degree of strain recovery of the hardened cement indicates better elasticity of the hardened cement.

In the method for measuring the elasticity of hardened cement for cementing of oil-gas wells, preferably, for the qualitative description of the mechanic integrity of the hardened cement, the hardened cement is subjected to a multi-cycle mechanic test by a testing method using alternating loadings; and if the hardened cement shows microcracks or breaks, the hardened cement cannot withstand the mechanical impacts from various subsequent engineering operations, indicating lack of mechanic integrity; or
  if the hardened cement does not show microcracks or break, the hardened cement can withstand the mechanical impacts from various subsequent engineering operations, indicating mechanic integrity.

According to a particular embodiment of the present invention, the data such as the loading rate, unloading rate, and maximum loading are determined by a true tri-axial mechanics apparatus (ZSZY-II, manufactured by ShanDong ShiYi Science and Technology Co. Ltd. of U.P.C).

The present invention further provides a device for measuring the elasticity of hardened cement for cementing of oil-gas wells, the device comprising:

a module for determining loading and unloading rates, which determines the loading and unloading rates of the hardened cement according to the force applied on the hardened cement and the duration required for the loading and unloading of the force in various engineering operations;
  a module for determining a maximum loading, which determines the maximum loading on the hardened cement by comparing the data of the force applied on the hardened cement in the various engineering operations to a normal stress-strain curve;
  a module for establishing a stress-strain curve, which establishes a stress-strain curve for the hardened cement by conducting a multi-cycle tri-axial stress test on the hardened cement at an experimental temperature and an experimental pressure based on the determined loading rate, unloading rate and maximum loading of the hardened cement; and an analytical module, which quantitatively describes the elasticity of the hardened cement with the degree of strain recovery of the hardened cement in different cycles, and qualitatively describes the mechanic integrity of the hardened cement with the degree of damage to the hardened cement in different cycles.

In the device for measuring the elasticity of hardened cement for cementing of oil-gas wells according to the present invention, preferably, the device further comprises a module for establishing a normal stress-strain curve, which establishes a normal stress-strain curve on the basis of a tri-axial stress test.

In the device for measuring the elasticity of hardened cement for cementing of oil-gas wells according to the present invention, preferably, the device further comprises a module for determining the maximum loading, which determines the average value of the maximum strains of the hardened cement, and determines the maximum loading as the stress value corresponding to the maximum strain according to the normal stress-strain curve.

In the device for measuring the elasticity of hardened cement for cementing of oil-gas wells according to the present invention, preferably, the device further comprises a module for determining the experimental temperature and experimental pressure, which determines the experimental temperature and the experimental pressure in accordance with the downhole depth of the hardened cement.

In the device for measuring the elasticity of hardened cement for cementing of oil-gas wells according to the present invention, preferably, in the analysis module, the degree of strain recovery of the hardened cement in different cycles is determined according to the following equation:

(maximum strain upon loading−minimum strain upon unloading)/maximum strain upon loading;

wherein the resultant value is the degree of strain recovery of the hardened cement, and a higher degree of strain recovery of the hardened cement indicates better elasticity of the hardened cement.

In the device for measuring the elasticity of hardened cement for cementing of oil-gas wells according to the present invention, preferably, in the analysis module, for the qualitative description of the mechanic integrity of the hardened cement, the hardened cement is subjected to a multi-cycle mechanic test by a testing method using alternating loadings; and
if the hardened cement shows microcracks or breaks, the hardened cement cannot withstand the mechanical impacts from various subsequent engineering operations, indicating lack of mechanic integrity; or
if the hardened cement does not show microcracks or break, the hardened cement can withstand the mechanical impacts from various subsequent engineering operations, indicating mechanic integrity.

In a tri-axial stress test, there is randomness in determining the loading and unloading rates with the instrument implementing existing measurement methods, while in the experimental means according to the present invention, the state of force application to the cement sheath in various engineering operations are fully considered, and the elasticity of the downhole cement sheath of oil-gas wells in post-cementing construction procedures can be more accurately reflected.

Young's modulus is the primary index currently used for evaluation of elasticity of hardened cement. However, different loading rates or different intervals taken from a stress-strain curve lead to lack of reproducibility and accuracy of the Young's modulus of hardened cement. According to the present invention, the degrees of strain recovery under alternating loadings in different cycles truly reflect the elasticity of various types of hardened cement, providing a universal comparing platform for research and development of special cement systems for oil-gas wells.

Current examination of the long-term mechanic integrity of hardened cement primarily depends on the data of uni-axial compression strength after curing at different temperatures and pressures, which cannot reflect the degree of mechanic damage to the cement sheath caused by post-cementing continuous engineering operations. The present invention conducts a tri-axial stress test on hardened cement under the condition of multi-cycles of pressure and a simulated actual downhole temperature, and can qualitatively and truly reflect the long-term mechanic integrity of the hardened cement.

The method for measuring elasticity of hardened cement for cementing of oil-gas wells according to the present invention develops a scientific fundamental theory for laboratories to elucidate the nature of mechanics of hardened cement in downhole environments, provides technical support for establishment of a measurement standard for the elasticity of hardened cement, provides measurement means for research and development of tough hardened cement, and eventually ensures the integrity of the entire well hole of an oil-gas well.

The method for measuring elasticity of hardened cement for cementing of oil-gas wells according to the present invention provides a universal comparing platform for research on hardened cement modification and for measurement of domestic and international special cement slurry systems, and provides a strong technical support for real representation of the nature of mechanics of a downhole cement sheath, which is of great significance in evaluation of the integrity of the well hole and the lifetime of a well.

DETAILED DESCRIPTION

For a better understanding of the technical features, objectives and beneficial effects of the present invention, description is provided in detail for the technical solutions of the invention, but is not intended to be construed as limiting the implementable scope of the present invention.

In the following Examples, an on-site sample taken from the cement slurry for well cementing in the 7-inch liner of the X gas well in the Chuanyu gas field (#1 the Tough Cement system, provided by the downhole operation division of the CNPC Chuanqing Drilling Engineering Company Ltd., density: 2.30 g/cm$^3$) and pure cement (Jiahua cement, grade water/cement ratio: 0.44, density: 1.90 g/cm$^3$) were used; curing conditions: at a temperature of 119° C. and pressure of 20.7 MPa.

Example 1

Figure 1:
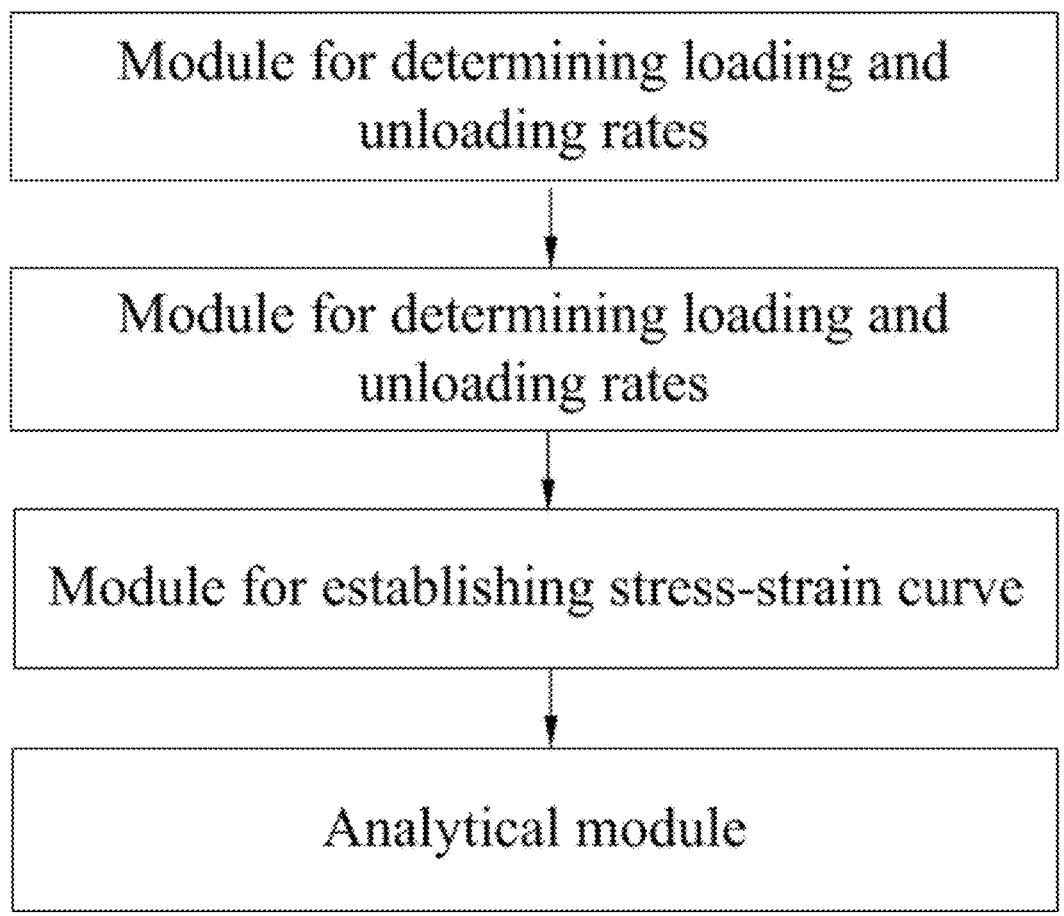
FIG. 1 is a structural schematic representation of a device for measuring the elasticity of hardened cement for cementing of oil-gas wells according to an example.

This example provides a device for measuring the elasticity of hardened cement for cementing of oil-gas wells. The device has a structure as shown in FIG. 1, and specifically comprises:

a module for determining loading and unloading rates, which determines the loading and unloading rates of the hardened cement according to the force applied on the hardened cement and on the duration required for the loading and unloading of the force in various engineering operations;

a module for determining a maximum loading, which determines the maximum loading on the hardened cement by comparing the data of the force applied on the hardened cement in the various engineering operations to a normal stress-strain curve;

a module for establishing a stress-strain curve, which establishes the stress-strain curve of the hardened cement by conducting a multi-cycle tri-axial stress test on the hardened cement at the experimental temperature and the experimental pressure based on the determined loading rate, unloading rate and maximum loading of the hardened cement; and an analytical module, which quantitatively describes the elasticity of the hardened cement with the degree of strain recovery of the hardened cement in different cycles, and qualitatively describes the mechanic integrity of the hardened cement with the degree of damage to the hardened cement in different cycles.

Figure 2:
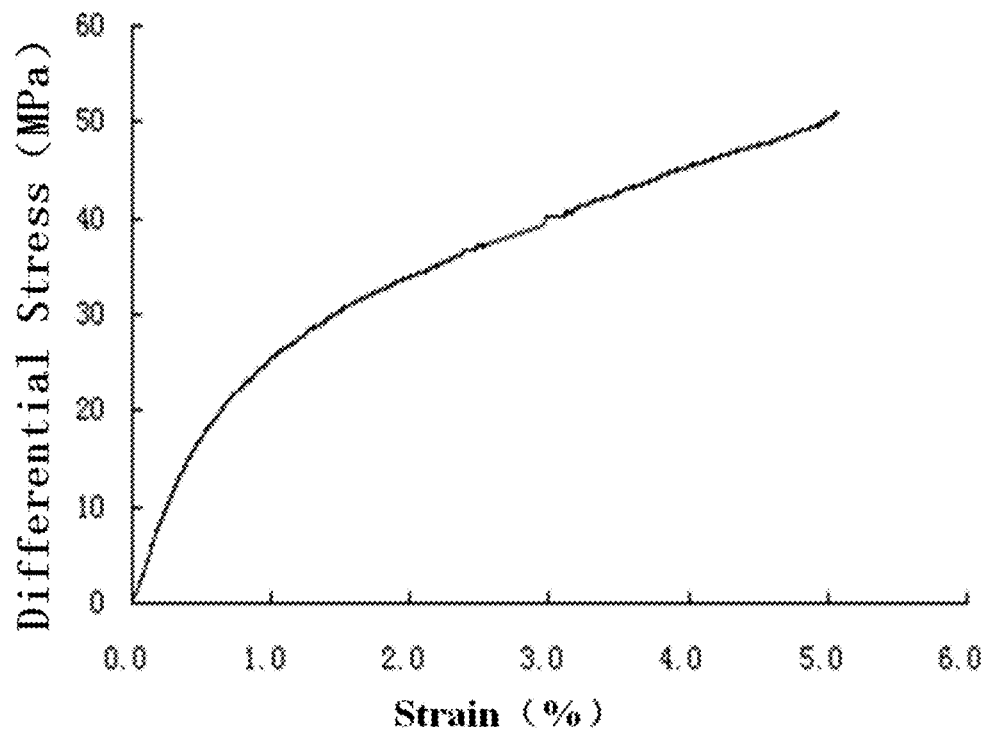
FIG. 2 is a graph of the stress-strain curve of pure cement according to an example.
Figure 3:
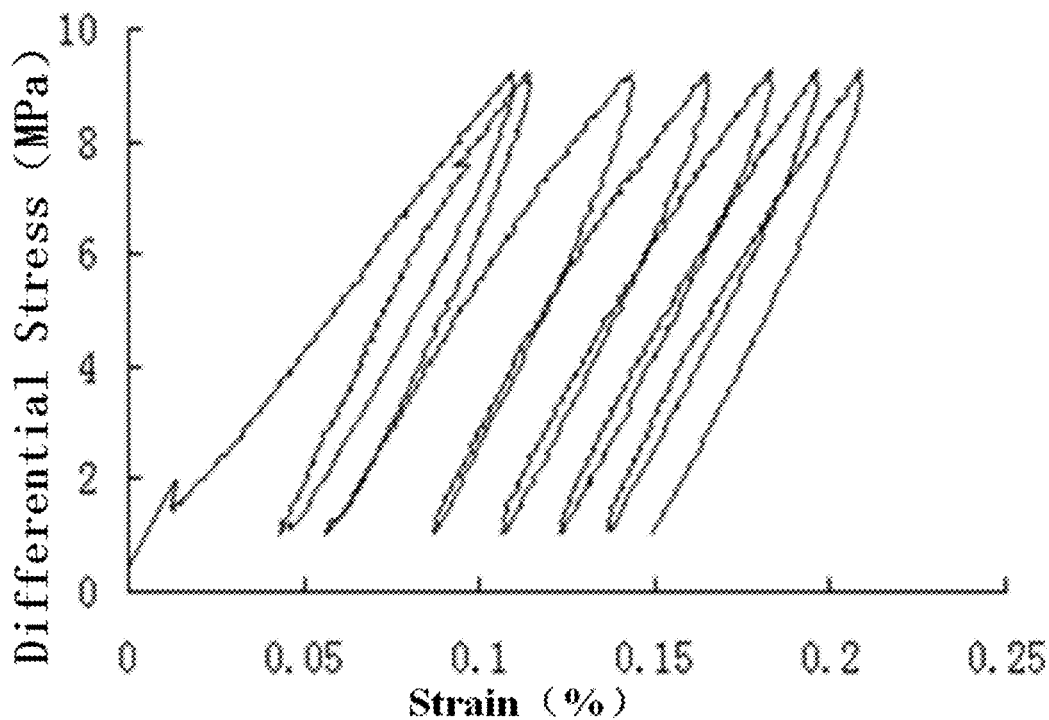
FIG. 3 is a graph of the stress-strain curve of pure cement according to an example under alternating loadings.
Figure 4:
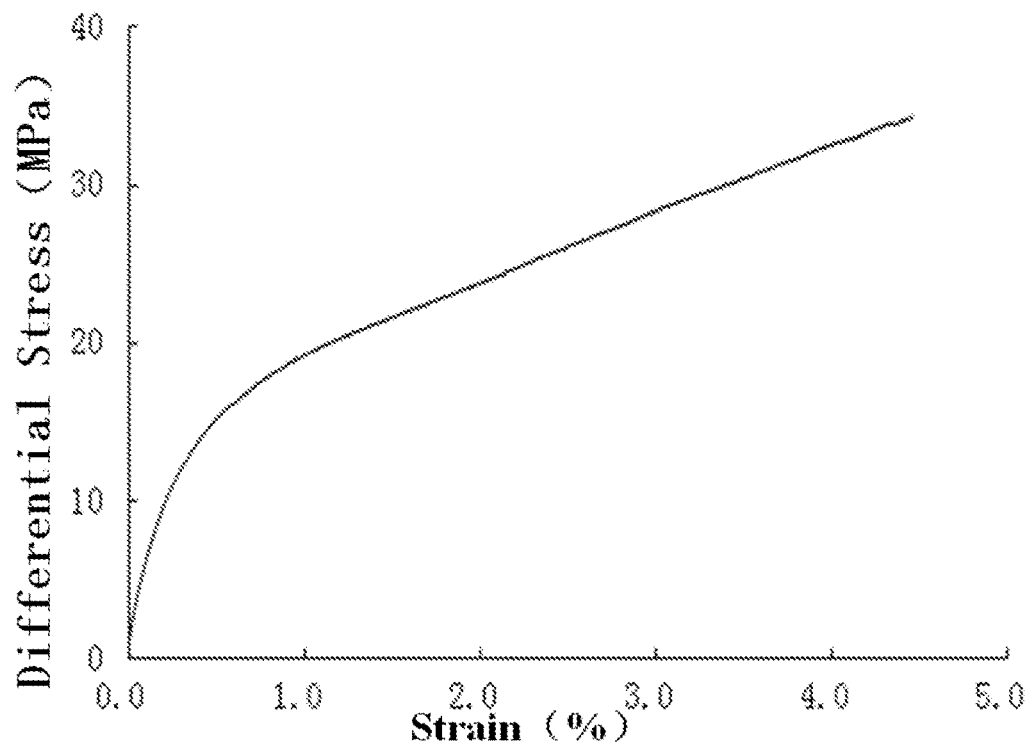
FIG. 4 is a graph of the stress-strain curve of #1 the Tough Cement according to an example.
Figure 5:
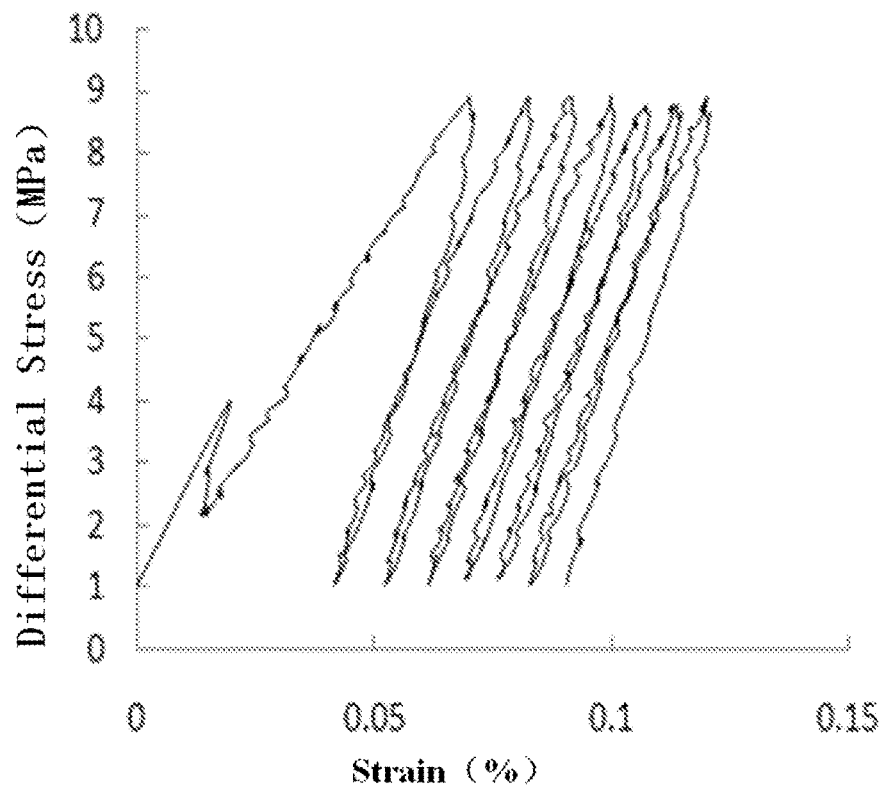
FIG. 5 is a graph of s the tress-strain curve of #1 the Tough Cement according to an example under alternating loadings.

This example provides a method for measuring the elasticity of hardened cement for cementing of oil-gas wells, specifically comprising the steps of:

taking cement bulk samples and on-site liquid from the well-cementing site;

preparing and curing the cement sampled on-site (slurry system of #1 the Tough Cement, density: 2.30 g/cm$^3$) and pure cement (water/cement ratio: 0.44, density: 1.90 g/cm$^3$) according to the API standard; upon completion of curing at a high temperature and high pressure (curing temperature: 119° C., curing pressure: 20.7 MPa, curing period: 7 days), taking the core or directly curing the cement with a standard rock core mold to prepare a hardened cement sample having a standard rock core size (φ25.4 mm×50.8 mm);

determining the loading and unloading rates: with the *Software System for Analysis of Formation Cement Sheath Mechanics* (Chinese Software Writing Registration No. 0910640) developed by the Southwest Oil&Gasfield Company, the loading and unloading rates were calculated as 1.6 kN/min and 3.2 kN/min, respectively, for the well cementing with a 177.8 mm casing at a well depth of 5000 m, with a drilling fluid at a density of 2.20 g/cm$^3$, and at a testing pressure of 30 MPa;

establishing a normal stress-strain curve: performing a tri-axial stress test on the pure cement and #1 the Tough Cement at a loading rate of 1.6 kN/min until the hardened cement was damaged, so as to obtain a normal stress-strain curve, as shown in FIGS. 2 and 4;

determining the maximum loading under alternating loadings: with the *Software System for Analysis of Formation Cement Sheath Mechanics* (Chinese Software Writing Registration No. 0910640), the maximum strain of the cement sheath was calculated as 0.1811% for the well cementing with a 177.8 mm casing at a well depth of 5000 m, with a drilling fluid at a density of 2.20 g/cm$^3$, and at a testing pressure of 30 MPa; and the corresponding stress values found in the graph of the stress-strain curve of the pure cement shown in FIG. 2 and in the graph of the stress-strain curve of Tough Cement 1 shown in FIG. 4 were 8.6 MPa and 8.7 MPa, respectively, which were used as the maximum loading of the alternating loadings; and establishing a stress-strain curve by conducting a tri-axial stress test under 6 cycles of alternating loadings on the pure cement and #1 the Tough Cement, with the loading rate of 1.6 kN/min and the unloading rate of 3.2 kN/min and the maximum loadings of 8.6 MPa and 8.7 MPa, respectively, as shown in FIGS. 3 and 5.

The degree of strain recovery of the hardened cement in each cycle was calculated according to the following equation: (maximum strain upon loading−minimum strain upon unloading)/maximum strain upon loading; which was used to compare and evaluate the elasticity/flexibility/toughness of the two hardened cements. Moreover, under the alternating loadings, the degree of damage to the hardened cements in different cycles (presence or absence of cracks or breaking on the hardened cement) was observed and used to compare and evaluate the long-term mechanic integrity of the two hardened cements.

FIGS. 3 and 5 are graphs of stress-strain curves of the pure cement and #1 the Tough Cement system from the tests under alternating loadings in consideration of the pressure-testing engineering operations (well cementing with a 177.8 mm casing at a well depth of 5000 m, with a drilling fluid at a density of 2.20 g/cm$^3$, and at a testing pressure of 30 MPa). As can be seen from the graphs, in each cycle both hardened cements underwent a process in which the strain decreases at various degrees with the decrease in the stress; in other words, both hardened cements showed certain elasticity (or flexibility or toughness) under alternating loadings. For a comparative analysis, the degree of strain recovery of the two hardened cements in each cycle was used to quantitatively describe the elasticity (or flexibility or toughness) thereof, and the degree of damage to the hardened cements occurring in each cycle was used to qualitatively describe the long-term mechanic integrity of the hardened cements.

1. Degree of Strain Recovery of the Hardened Cement

From the curves in FIGS. 3 and 5, the degrees of strain recovery of the pure cement in the 6 cycles of alternating loadings were 0.072, 0.067, 0.061, 0.056, 0.051, and 0.050, respectively; the degrees of strain recovery of #1 the Tough Cement in 5 cycles of alternating loadings were 0.0461, 0.0561, 0.0593, 0.0572, and 0.0609, respectively. #1 the Tough Cement was damaged in the 6$^{th}$ cycle of alternating loadings.

(1) When the degrees of strain recovery of the hardened cements in the $1^{st}$ cycle are compared, #1 the Tough Cement had a lower degree of strain recovery than that of the pure cement, which did not mean that the elasticity or flexibility or toughness of the pure cement was better than that of #1 the Tough Cement. Upon analysis, it is believed that the pure cement was a hardened cement having a regular density of 1.90 g/cm³ formulated with a grade G cement for oil wells at a water/cement ratio of 0.44 (its engineering properties, including stability, thickening time and the like, do not meet relevant regulations and requirements) and having poor settling stability, and therefore the hardened cement formed was relatively dense, and directly entered the elasticity/flexibility/toughness deformation phase during loading. In contrast, for #1 the Tough Cement, because various external additives for enhancing toughness, elasticity, or flexibility were added in the system of #1 the Tough Cement in consideration of the overall engineering performance, and the stable system resulted in a certain pore space within the formed crystalline structure, there was a compressed phase during the initial loading and unloading, which phase did not reflect the mechanic deformation capacity in terms of the elasticity/flexibility/toughness of the system. As seen at later stages, starting from the $4^{th}$ cycle, the degree of strain recovery of #1 the Tough Cement became higher than that of the pure cement.

(2) Based on the results from alternating loadings, the result of comparison of the elasticity of the two hardened cements is: hardened #1 the Tough Cement>hardened pure cement.

2. Degree of Damage to the Hardened Cement

As observed during the test of the two hardened cements under alternating loadings, #1 the Tough Cement became damaged in the $6^{th}$ cycle of alternating loadings, showing the result of comparison of the long-term mechanic integrity of the two hardened cements: hardened pure cement>hardened #1 the Tough Cement.

Example 2

Figure 6:
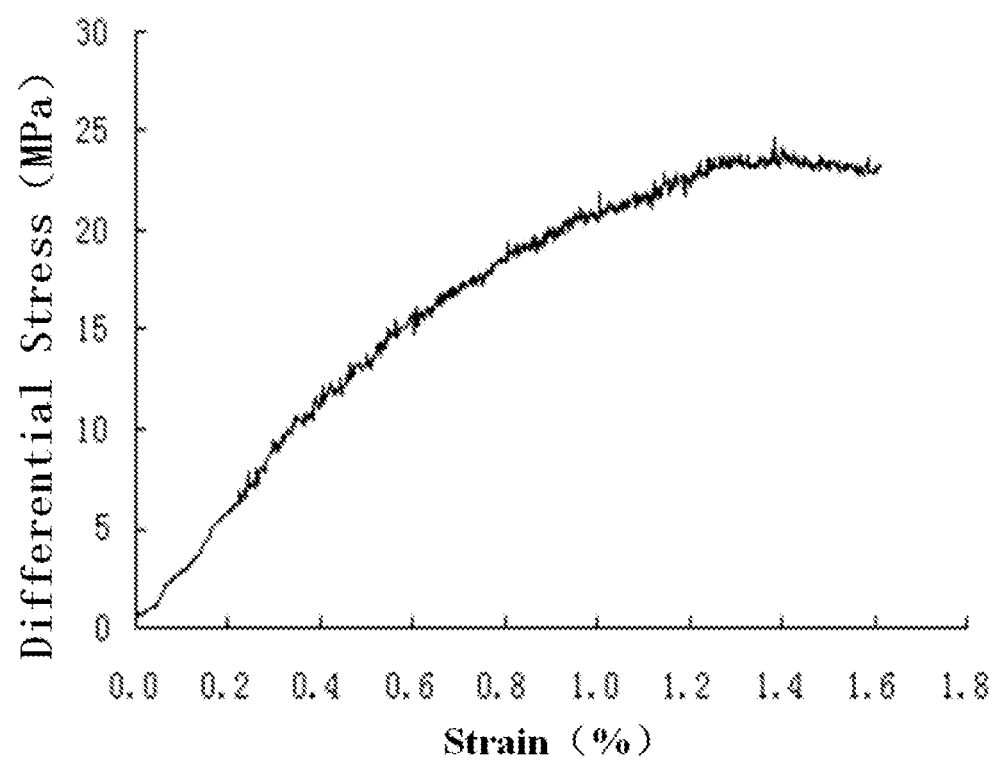
FIG. 6 is a graph of the stress-strain curve of #2 the Micro Expansive Cement according to an example.
Figure 7:
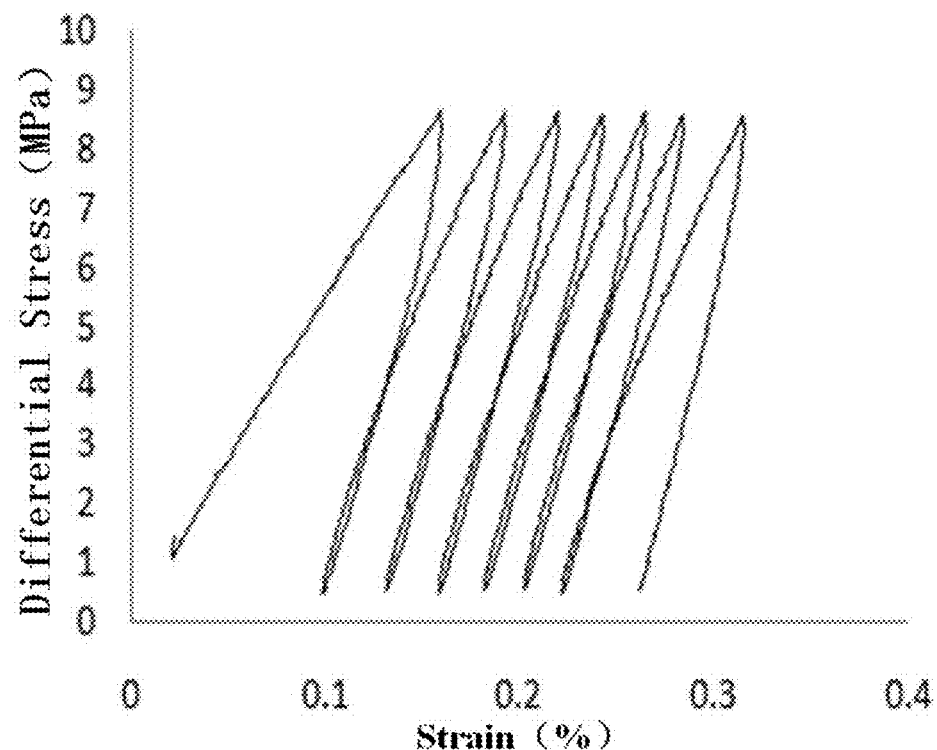
FIG. 7 is a graph of the stress-strain curve of #2 the Micro Expansive Cement according to an example under alternating loadings.
Figure 8:
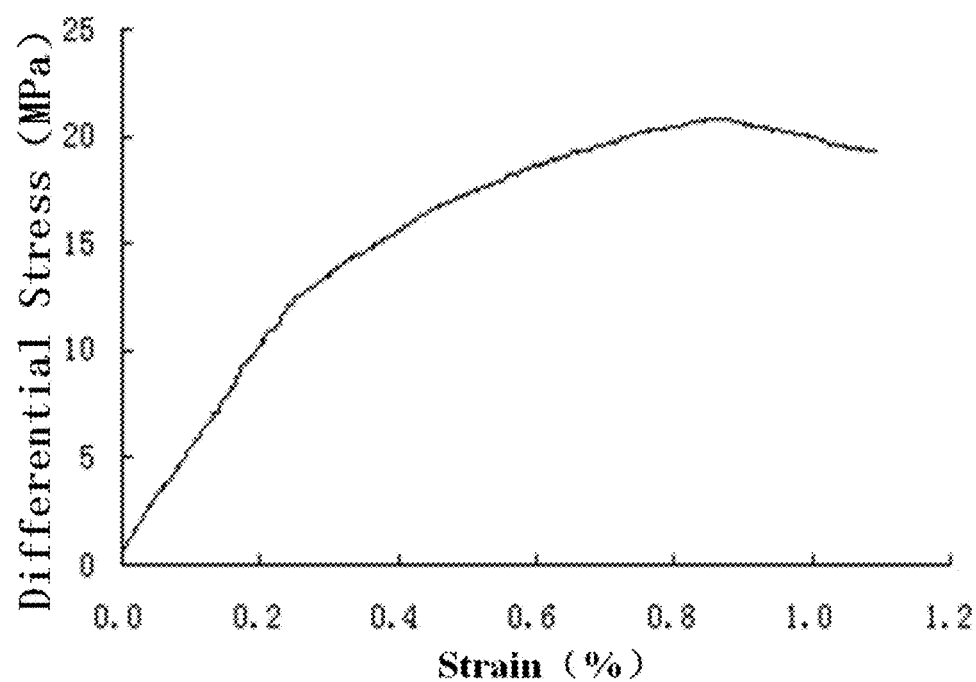
FIG. 8 is a graph of the stress-strain curve of #3 the Elastic Cement according to an example.
Figure 9:
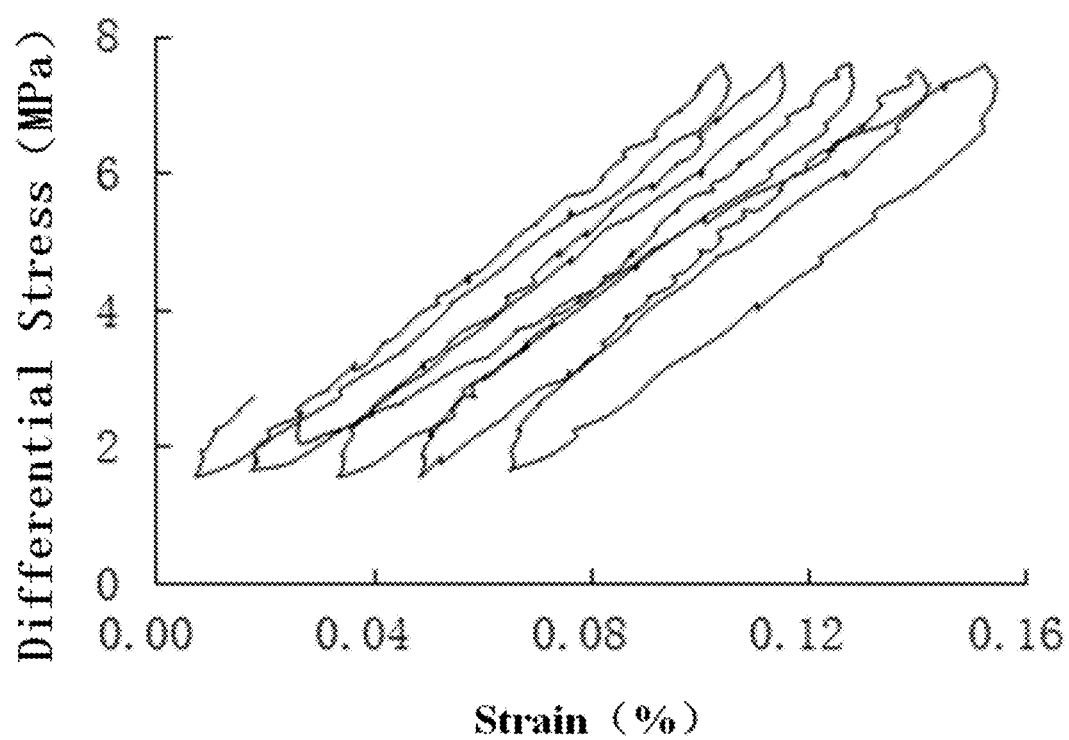
FIG. 9 is a graph of the stress-strain curve of #3 the Elastic Cement according to an example under alternating loadings.

This example provides a method for measuring the elasticity of hardened cement for cementing of oil-gas wells, specifically comprising the steps of:
taking cement bulk samples and on-site liquid twice from the well-cementing site of the injection-production well at the gas storage (a system of #3 the Elastic Cement, provided by Schlumberger Ltd.; and a system of #2 the Micro Expansive Cement, provided by the CNPC Engineering Technology R&D Company Ltd.);
preparing and curing the cement sampled on-site (#3 the Elastic Cement, density: 1.75 g/cm³, and #2 the Micro Expansive Cement, density: 1.75 g/cm³) according to the API standard; upon completion of curing at a high temperature and high pressure (curing temperature: 58° C., curing pressure: 20.7 MPa, curing period: 7 days), taking the core or directly curing the cement with a standard rock core mold to prepare hardened cement samples with a standard rock core size (φ25.4 mm×50.8 mm);
determining the loading and unloading rates: with the *Software System for Analysis of Formation Cement Sheath Mechanics* (Chinese Software Writing Registration No. 0910640) developed by the Southwest Oil&Gas field Company, the loading and unloading rates were calculated as 0.5 kN/min and 2.0 kN/min respectively, for the well cementing with a 177.8 mm casing at a well depth of 3000 m, with gas production of 60×10⁴ m³/d and gas injection of 90×10⁴ m³/d;
establishing a normal stress-strain curve: performing a tri-axial stress test on #2 the Micro Expansive Cement and #3 the Elastic Cement at a loading rate of 0.5 kN/min until the hardened cement was damaged, so as to obtain a normal stress-strain curve, as shown in FIGS. 6 and 8;
determining the maximum loading under alternating loadings: with the Software System for Analysis of Formation Cement Sheath Mechanics (Chinese Software Writing Registration No. 0910640), the maximum strain of the cement sheath was calculated as 0.1624% for the well cementing with 177.8 mm casing at a well depth of 3000 m, with gas production of 60×10⁴ m³/d and gas injection of 90×10⁴ m³/d, and the corresponding stress values found in the graph of the stress-strain curve of #2 the Micro Expansive Cement shown in FIG. 5 and in the graph of the stress-strain curve of #3 the Elastic Cement shown in FIG. 7 were 8.5 MPa and 7.8 MPa, respectively, which were used as the maximum loading of the alternating loadings; and
establishing a stress-strain curve by conducting a tri-axial stress test under 6 cycles of alternating loadings on #2 the Micro Expansive Cement and #3 the Elastic Cement, with the loading rate of 0.5 kN/min and the unloading rate of 2.0 kN/min and the maximum loadings of 8.5 MPa and 7.8 MPa, respectively, as shown in FIGS. 7 and 9.

The degree of strain recovery of the hardened cement in each cycle was calculated according to the following equation: (maximum strain upon loading−minimum strain upon unloading)/maximum strain upon loading; which was used to compare and evaluate the elasticity/flexibility/toughness of the two hardened cements. Moreover, under the alternating loadings, the degree of damage to the hardened cements in different cycles (presence or absence of cracks or breaking on the hardened cement) was observed and used to compared and evaluate the long-term mechanic integrity of the two hardened cements.

1. Degree of Strain Recovery of the Hardened Cement

From the curves in FIGS. 7 and 9, the degrees of strain recovery of #2 the Micro Expansive Cement in the 6 cycles of alternating loadings were 0.0681, 0.768, and 0.074, respectively, with cracks appearing in the $4^{th}$ cycle of alternating loadings; the degrees of strain recovery of #3 the Elastic Cement in 6 cycles of alternating loadings were 0.0842, 0.082, 0.082, 0.067, 0.0784, and 0.0762 respectively; #3 the Elastic Cement maintained its integrity and had a higher degree of strain recovery than that of #2 the Micro Expansive Cement during first three cycles of alternating loadings.

Based on the results from alternating loadings, the result of comparison of the elasticity of the two hardened cements is: #3 the Elastic Cement>#2 the Micro Expansive Cement.

2. Degree of Damage to the Hardened Cement

As observed during the test of the two hardened cements under alternating loadings, in #2 the Micro Expansive Cement became damaged in the $3^{th}$ cycle of alternating loadings, while #3 the Elastic Cement maintained its integrity after the 6 cycles of alternating loadings, showing the result of comparison of the long-term mechanic integrity of the two hardened cements: #3 the Elastic Cement>#2 the Micro Expansive Cement.

The system, device, module, or unit as illustrated in the above Examples can be implemented by a computer chip or entity, or implemented by a product with a certain function.

For the ease of description, various modules defined by function are separately described for the above device. However, the functions of the various modules can certainly be implemented in one or more than one piece of software and/or hardware when the present invention is implemented.

Based on the description of the above embodiments, those skilled in the art may clearly understand that the present invention can be implemented by means of software in combination with a general hardware platform. Based on such understanding, it is possible to embody the essence of the technical solutions of the present application or the part making a contribution over the prior art in the form of a software product, and in a typical configuration, a computing device includes one or more processors (CPU), an input/output interface, a network interface and a memory.

Each of the examples in the specification is described in a progressive manner, with the same or similar parts in each of the examples referential to each other, and the part that distinguishes an example from other example(s) is described by emphasis. In particular, for an example of system, description is relatively concise because it is similar to an example of method, and reference can be made to the counterpart described in the example of method.

The present application can be described in the general context of computer executable instructions executed by a computer, such as a program module. Generally, a program module includes a routine, a program, an object, a component, a data structure or the like that executes a particular task or embody a particular type of abstract data. The present application may also be practiced in a distributed computing environment where a remote processing device connected by communication networks executes the task. In a distributed computing environment, a program module may be located in the local and remote computer storage media including a storage device.

As demonstrated in the above examples, the method and device for measuring the elasticity of hardened cement for cementing of oil-gas wells according to the present invention provide a universal comparing platform for research on hardened cement modification as well as examination of domestic and international special cement slurry systems, and provides a strong technical support for real representation of the nature of mechanics of the downhole cement sheath, which is of great significance in evaluation of the integrity of the well hole and the lifetime of a well.

The invention claimed is:

1. A method for measuring the elasticity and mechanical integrity of hardened cement for cementing of oil-gas wells, the method comprising the steps of:
   i) determining the loading and unloading rates of the hardened cement, according to the force applied on the hardened cement and the duration required for the loading and unloading of the force, in various engineering operations;
   ii) establishing a normal stress-strain curve, and determining the maximum loading on the hardened cement by comparing the data of the force applied on the hardened cement in the various engineering operations to the normal stress-strain curve;
   iii) determining the experimental temperature and the experimental pressure, and establishing a stress-strain curve for the hardened cement by conducting a multi-cycle tri-axial stress test on the hardened cement at the experimental temperature and the experimental pressure based on the determined loading rate, unloading rate and maximum loading of the hardened cement; and obtaining a quantitative evaluation of the elasticity of the hardened cement with the degree of strain recovery of the hardened cement in different cycles; and
   iv) obtaining a qualitative evaluation of the mechanic integrity of the hardened cement by conducting a multi-cycle mechanic test by a testing method using alternating loadings.

2. The method according to claim 1, characterized by further comprising a step of preparing an experimental sample of hardened cement, prior to the measurement of the elasticity of the hardened cement for cementing of oil-gas wells, the preparing comprising:
   preparing an experimental cement slurry, setting and hardening the cement slurry into hardened cement by curing the cement slurry under a simulated temperature and pressure condition for hardened cement for a designated period of time according to the downhole environment surrounding the hardened cement, and processing the hardened cement to a standard core size to obtain the sample of hardened cement.

3. The method according to claim 1, characterized in that the normal stress-strain curve is established through a tri-axial stress test.

4. The method according to claim 1, characterized in that the determining the maximum loading on the hardened cement comprises the step of:
   determining the average value of the maximum strains of the hardened cement, and determining the maximum loading as the stress value corresponding to the maximum strain according to the normal stress-strain curve.

5. The method according to claim 1, characterized in that the experimental temperature and the experimental pressure are determined in accordance with the downhole depth of the hardened cement.

6. The method for according to claim 1, characterized in that the degree of strain recovery of the hardened cement in different cycles is determined according to the following equation:

(maximum strain upon loading−minimum strain upon unloading)/maximum strain upon loading.

7. The method according to claim 1, characterized in that for the qualitative evaluation of the mechanic integrity of the hardened cement,
   if the hardened cement shows microcracks or breaks, the hardened cement cannot withstand the mechanical impacts from various subsequent engineering operations, indicating lack of mechanic integrity; or
   if the hardened cement does not show microcracks or break, the hardened cement can withstand the mechanical impacts from various subsequent engineering operations, indicating mechanic integrity.

* * * * *